United States Patent
Arfaj et al.

(10) Patent No.: US 12,144,707 B2
(45) Date of Patent: Nov. 19, 2024

(54) SMART HEARING PROTECTION DEVICE

(71) Applicant: SAUDI ARABIAN OIL COMPANY, Dhahran (SA)

(72) Inventors: Ayman M. Arfaj, Dhahran (SA); Hassan A. Al Khunaizi, Dhahran (SA); Salim A. Khasawinah, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 149 days.

(21) Appl. No.: 17/646,430

(22) Filed: Dec. 29, 2021

(65) Prior Publication Data

US 2023/0201040 A1 Jun. 29, 2023

(51) Int. Cl.
| | |
|---|---|
| H04R 29/00 | (2006.01) |
| A61F 11/14 | (2006.01) |
| G01H 17/00 | (2006.01) |
| G08B 5/38 | (2006.01) |
| G08B 6/00 | (2006.01) |

(52) U.S. Cl.
CPC ........... *A61F 11/145* (2022.01); *G01H 17/00* (2013.01); *G08B 5/38* (2013.01); *G08B 6/00* (2013.01); *H04R 29/00* (2013.01); *H04R 29/008* (2013.01)

(58) Field of Classification Search
CPC ................. H04R 1/1083; H04R 1/1008; H04R 2460/01; H04R 29/00; H04R 29/008; A61F 11/45
USPC ...................................................... 381/72, 56
See application file for complete search history.

(56) References Cited

U.S. PATENT DOCUMENTS

| | | | |
|---|---|---|---|
| 8,705,787 B2* | 4/2014 | Larsen ................ | H04R 1/1016 381/328 |
| 10,068,451 B1* | 9/2018 | Werner ................ | H04R 29/00 |
| 10,109,172 B1* | 10/2018 | Werner ................ | G08B 21/02 |
| 11,260,251 B2* | 3/2022 | Awiszus ................ | A42B 3/225 |
| 11,265,644 B2* | 3/2022 | Kara ..................... | H04R 1/1066 |
| 11,317,225 B2* | 4/2022 | Karamuk ............. | H04R 25/652 |
| 11,706,559 B2* | 7/2023 | Henry ................... | A61F 11/08 128/867 |
| 11,722,813 B2* | 8/2023 | Keikhosravy ......... | H04R 3/005 381/74 |
| 2019/0090044 A1* | 3/2019 | Boesen ................ | G10K 11/175 |

* cited by examiner

*Primary Examiner* — Disler Paul
(74) *Attorney, Agent, or Firm* — Osha Bergman Watanabe & Burton LLP

(57) ABSTRACT

A smart hearing protection (SHP) device operatively connected to a human ear is disclosed. An internal sensor disposed on an inner side of the SHP device is configured to measure sound pressure level exposure of the human ear. An external sensor disposed on an outer side of the SHP device is configured to measure a sound pressure level external to the SHP device. The SHP includes a wireless transmitter operatively connected to both the internal and external sensors for transmitting data to a smart hearing software application for storing sensor data and monitoring sound pressure levels in connection with occupational safety and health.

6 Claims, 4 Drawing Sheets

SMART HEARING PROTECTION DEVICE

BACKGROUND

In many situations, noise is considered one of the major occupational health risks in oil and gas industries. The fields of industrial hygiene and occupational health are concerned with the protection of human health during routine and non-routine jobs. Protection of valuable assets is done by large oil and gas companies by ensuring environmental and health compliance and ongoing monitoring assessments with environmental and health regulations. Accordingly, there exists a need for a hearing protection device that shares its measurement data via software with the environmental and health regulation agencies to ensure compliance.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a smart hearing protection (SHP) device operatively connected to a human ear, including an internal sensor disposed on an inner side of the SHP device and configured to measure sound pressure level exposure of the human ear, an external sensor disposed on an outer side of the SHP device and configured to measure a sound pressure level external to the SHP device, and a wireless transmitter operatively connected to both the internal and external sensors for transmitting data to a smart hearing software application for storing sensor data and monitoring sound pressure levels in connection with occupational safety and health.

In one aspect, embodiments disclosed herein relate to a method, involving wearing, by a user, a smart hearing protection (SHP) device, wherein the SHP device is operatively connected to an ear of the user, and wherein the user is located in a harsh industrial environment with high noise levels, measuring, by at least one internal sensor disposed on an inner side of the SHP device, a sound pressure exposure level inside the ear of the user, wirelessly transmitting the measured sound pressure exposure level to a smart hearing software application, comparing the measured sound pressure exposure level to a sound pressure level safety threshold, determining whether the measured sound pressure exposure level exceeds the sound pressure level safety threshold based on the comparison, and sending an alert signal to the SHP device, when the measured sound pressure exposure level exceeds the sound pressure level safety threshold.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In one aspect, embodiments disclosed herein relate to a smart hearing protection device that which gathers the actual sound pressure level in dB(A) (i.e., the noise level) from a noise source through two smart sensors (internal and external) to compare the effectiveness of Noise Reduction Rating (NRR) of the hearing protection to monitor the actual exposure. The device has an integrated alarm system that will alert users if used improperly or if sound pressures are above set limits. Smart hearing protection is connected through wireless functionality to software to analyze data more accurately and evaluate through the implementation & utilization of technology.

Embodiments of the present disclosure may provide at least one of the following advantages. Embodiments disclosed herein bolster the competency of Industrial Hygiene Professionals to gather and analyze real-time noise data (i.e. personnel exposure to noise), with effective monitoring and governance mechanism. Specifically, embodiments disclosed herein combine and utilize two smart noise sensors that are attached to ear plugs/ear muffs internal and external to the human ears. All this information (data) will be displayed and connected to software that can by analyzed by Industrial Hygienist and Occupational Health Specialist in order to monitor any potential noise hazard. Furthermore, the data will be mobilized into machine learning and artificial intelligence solutions in order to automate the process of providing a technical industrial hygiene judgement.

Figure 1:
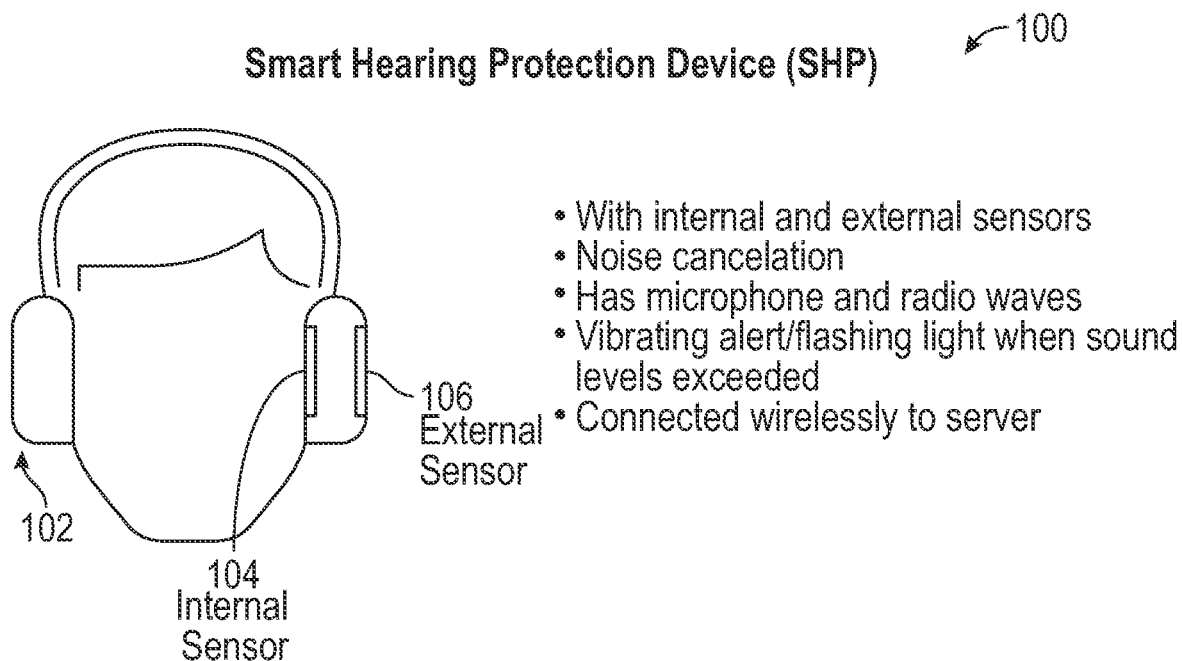
FIG. 1 shows a smart hearing protection (SHP) device in accordance with one or more embodiments.

FIG. 1 shows a smart hearing protection (SHP) device (100) in accordance with one or more embodiments. In one or more embodiments, the SHP device works as sound-level meter to display, to interested personnel, noise level readings in dB(A). The SHP device may include two ear muffs (102) or ear plugs or any other suitable over- or in-ear wearable device capable of housing at least two sensors. The SHP device may be over the head headphones as shown, or may be in-ear device such as the wireless ear plug devices known in the art. In one or more embodiments, the sensors include an internal sensor (104) and an external sensor (106). The internal sensor (104) is disposed inside of the ear muff (i.e., on an inner side against the human ear), ear plug, or other ear device and may be any suitable wireless sensor capable of measuring decibel levels (dBA) of the noise level inside the ear. The internal sensor (104) enables measuring the sound pressure inside the hearing protection device.

The external sensor (106) is disposed on an outer side of the ear muff, ear plug, or other wearable ear device. The external sensor (106) may also be any suitable wireless sensor capable of measuring decibel levels (dBA) of the noise level exterior to the SHP device (i.e., in the external environment which the user is exposed to). In one or more embodiments, the external sensor is any suitable a low cost sensor, such as MEMS-based sensor.

The SHP device (100) gathers the actual sound pressure level in dB(A) (i.e., the noise level) from a noise source through two the smart sensors (internal and external) to compare the effectiveness of Noise Reduction Rating (NRR) of the hearing protection to monitor the actual exposure. The noise source (not shown) may be any industrial machinery in the oil and gas industry such as, but not limited to, rig equipment on an oil rig, truck traffic, drilling, hydraulic fracturing, completion activities, production well pumps and air compressors. These noise sources have different frequencies, durations, and overall sound pressure levels that make it difficult to control. Those skilled in art will appreciate that the SHP device may also be used in other harsh industrial conditions outside of the oil and gas industry, such as, for example, in the music industry.

In one or more embodiments, the wireless connectivity of the SHP device (100) enables connections of the device to any external computing device (e.g., computing device 500 of FIG. 5), such as a PC, a server, a smart phone or a smart watch or other wearable device.

Those skilled in the art will appreciate that while two ear muffs or ear plug devices are shown in FIG. 1, embodiments disclosed herein may be implemented with a single ear muff or ear plug device. Further, the internal and external sensors may be the same type of sensor or different types of sensors capable of measuring a noise level/sound pressure. In addition, those skilled in the art will appreciate that while the internal and external sensors are shown in FIG. 1 on only one side of the SHP device, both ear muffs or in-ear inserts may include an internal and an external sensor as described without departing from the scope disclosed herein.

In one or more embodiments, the SHP device includes noise cancelling technology to protect hearing from the surrounding noisy environment. In addition, the SHP device has 2-way radio reception (e.g. communication with control center without removing the hearing protection especially in high noise areas) and microphone capability for communication with the control center.

In one or more embodiments, internal noise sensors (104) are used to measure noise at low level (i.e. it should be less than 85 dB(A)). Internal sensors (104) measure the noise after cancellation as the purpose is to measure the noise received by the ear. External noise sensors (106) are used to measure noise at high level (i.e. usually more than 85 dB(A)). In the oil and gas industry, noise levels in the harsh environment may exceed 115 db. The high noise level may be low or high frequency. The predominant industrial noise in oil and gas industry is high frequency noise.

Figure 2:
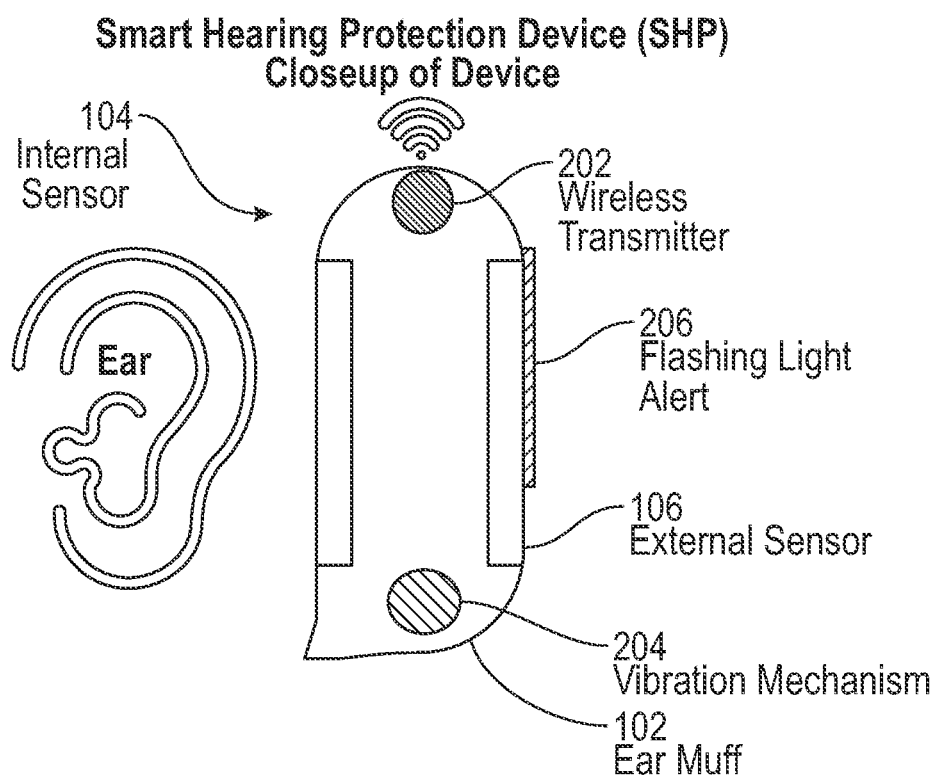
FIG. 2 shows an expanded view of the SHP components of the SHP device of FIG. 1 in accordance with one or more embodiments.

FIG. 2 shows an expanded view of the components of the SHP device in accordance with one or more embodiments. FIG. 2 shows, as part of the ear muff (102) or ear plug, the internal sensor (104), the external sensor (106), a wireless transmitter (202), and an alert mechanism (204, 206).

The wireless transmitter (202) may be used to transmit measured sensor data by both the internal and external sensors (104, 106) to a connected computing system executing software for health and safety compliance in oil field environments or any harsh environment where long-term exposure to loud noises may occur.

In one or more embodiments, the SHP device has an integrated overexposure alerting mechanism. Specifically, through either vibration (204) or flashing light (206), or both, the SHP device provides an alert to users if it is not worn properly. The vibration mechanism (204) may be any mechanism capable of vibrational haptic feedback. The light (206) may be an LED Also, an alert is provided if the sound pressure levels detected by the internal sensor exceed the specified limits. This removes the need to have another component for feedback and the device can fully function in a standalone fashion.

Figure 3:
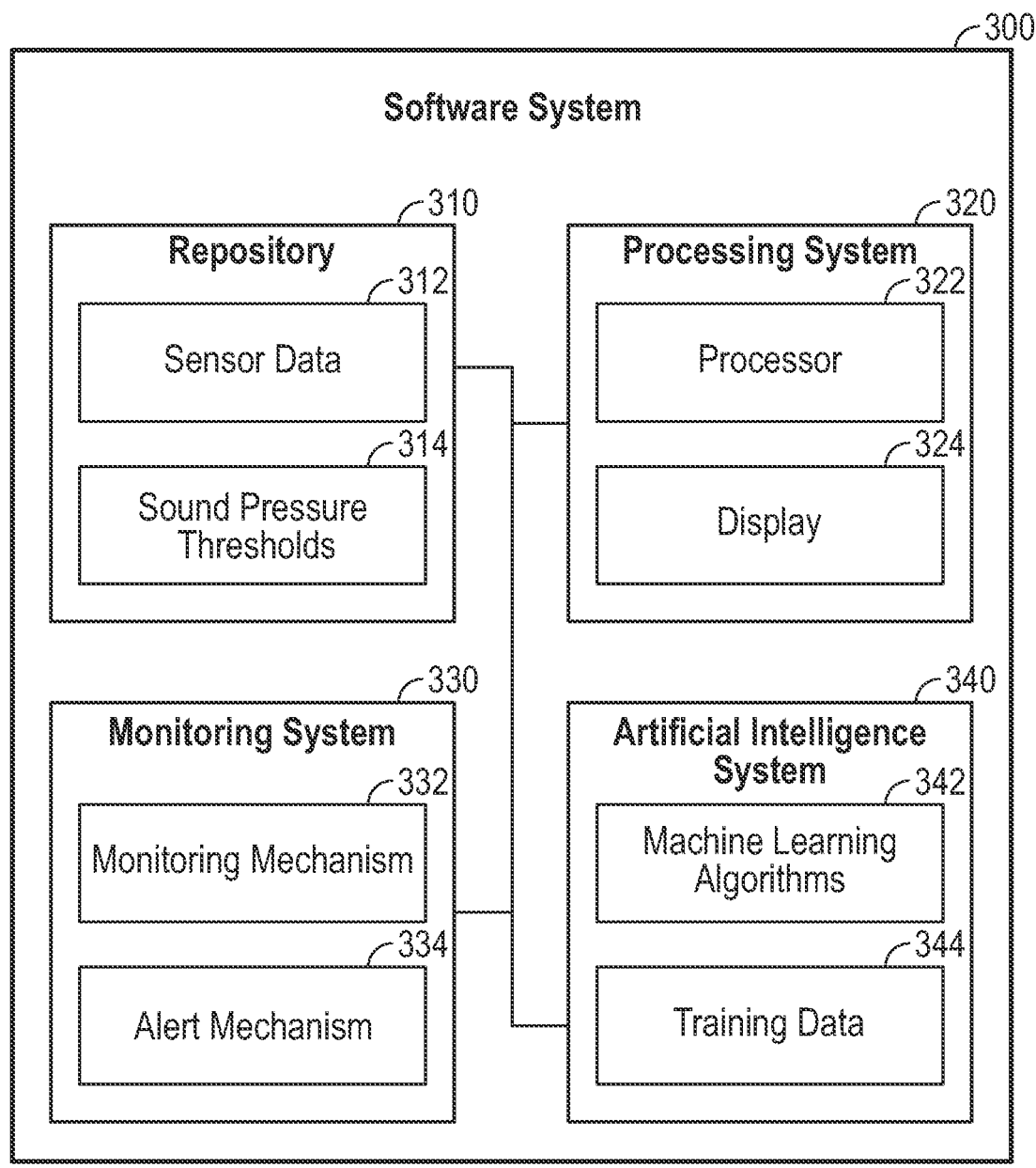
FIG. 3 shows a software system in accordance with one or more embodiments.

FIG. 3 shows a smart hearing software system (300) in accordance with one or more embodiments. In one or more embodiments, the smart hearing software system (300) is operatively connected to the SHP device shown in FIGS. 1 and 2. Communication between the software system (300) and the SHP (100) may be via a wireless protocol based on Wireless Local Area Network (WLAN) using wireless access points to connect to the wired network. Such a configuration with WLAN access points provides sufficient range and coverage. The smart hearing software system (300) may run on a remote server in the cloud computing environment, a remote server housed in a control center, or any other computing device, such as that shown in in FIG. 5 below. The smart hearing software system (300) includes, in one or more embodiments, a repository (310), a processing system (320), a monitoring system (330), and an artificial intelligence (AI) system (340). Each of these systems is described in detail below.

The repository (310) may be any database or data structure capable of storing data. In particular, the repository (310) stores sensor data (312) measured and wirelessly transmitted from the internal and external sensors on the SHP device. The repository may also store data regarding acceptable sound pressure thresholds (314) for health and safety standards of noise protection.

The processing system (320) includes a processor (322) for comparing sensor data (312) to the sound pressure thresholds (314). In one or more embodiments, measurements (acoustic) are be displayed on the display screen (324) in dB(A) in order to monitor measurements, record data and assess recommended sound exposure limits. The software system (300) works as sound-level meter to display to personnel noise level readings in dB(A).

The monitoring system (330) includes a monitoring mechanism (332) for monitoring the data displayed on the display (324) and an alerting mechanism (334) to alert personnel in case of over exposure to noise levels according to noise regulations. The monitoring mechanism may continuously or periodically monitor comparison results displayed on the display (324) or may communicate directly with the internal and external sensors of the SHP device to monitor sound level exposures.

Those skilled in the art will appreciate that the software system may be updated with data from the internal and external sensors of the SHP device in real-time. Accordingly, in one or more embodiments, the AI system (340) is configured to use the data stored in the repository as training data (344) which is used as input into the machine learning (ML) algorithms (342) which learn when sound pressure levels are unsafe or unhealthy for a user of the SHP device. In one or more embodiments, the sensor data (312) is mobilized into machine learning and artificial intelligence solutions in order to automate the process of providing a technical industrial hygiene judgement. The industrial hygiene judgement/knowledge is from the perspective of a technical practitioner in the field of oil and gas. In one or more embodiments, initially, a supervised or semi-supervised AI or machine learning (ML) algorithms (342) may be used to inform the proper decision. Further, it is envisioned that trained unsupervised ML algorithms may also be used. The software/AI is trained to detect and compare noise levels measured by the sensors with pre-defined levels. For example, 85 dB(A) in most cases would be considered too high and may be used as a threshold level for the internal sensor measurement. Moreover, through supervised learning, new levels to compare against may be added.

In one or more embodiments, the training of the machine learning models is a process to determine these parameters by optimizing the match between model prediction and the data. The supervised or unsupervised ML algorithms (342) may include neural network algorithms, Naive Bayes, Decision Tree, vector-based algorithms such as Support Vector Machines, or regression-based algorithms such as linear regression, etc. For example, the mathematical model may be an artificial neural network (ANN), where the model parameters correspond to weights associated with connections in the ANN.

Figure 4:
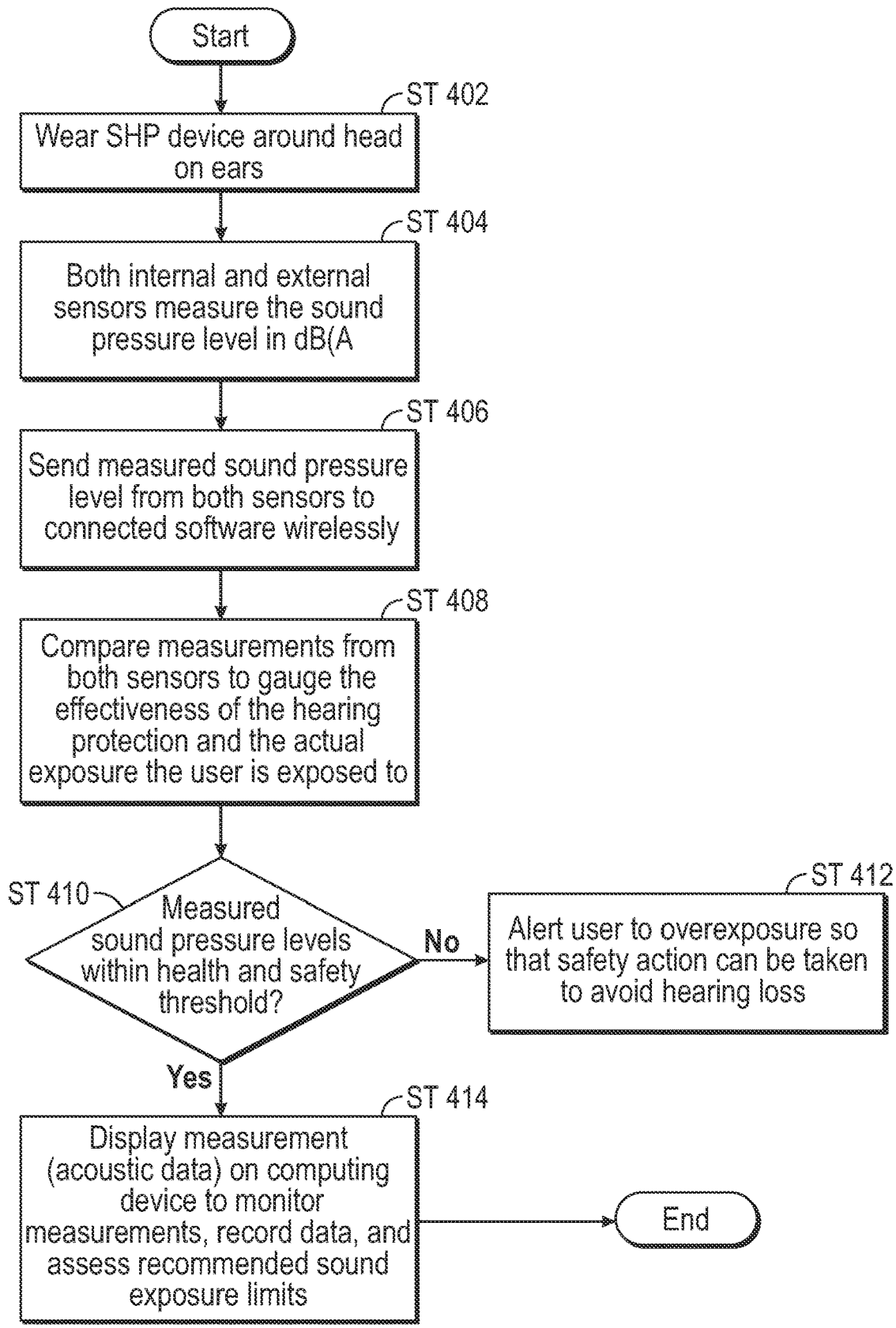
FIG. 4 shows a flowchart in accordance with one or more embodiments.

FIG. 4 shows a flowchart in accordance with one or more embodiments. Specifically, FIG. 4 describes a general method for determining exposure levels to noise in a harsh environment. One or more blocks in FIG. 3 may be performed by one or more components as described in FIGS. 1-3. While the various blocks in FIG. 4 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Initially, the user or field engineer exposed to harsh sound conditions wears the SHP device (Step 402). As described above, the SHP device may be any in-ear or over the ear headphones. While the device is worn or inserted, both the internal and external sensors embedded in the SHP device measure the sound pressure level in dB(A) from inside the ears and from the external environment (Step 404). The measured resound pressure levels are subsequently transmitted wirelessly to software executing on a computing device (Step 406). The software may be executed and analyzed by occupational health specialists that includes the standard measurements which are acceptable for personnel working or otherwise present in harsh environmental conditions.

In Step 408, the measurements (sound pressure levels in dBA) from both sensors are compared to standard acceptable levels stored in the software applications running on a computing device operatively connected to the SHP device in order to know the effectiveness of the hearing protection, the actual exposure that personnel is exposing to, and preventing any potential hearing loss.

At this stage a determination is made (Step 410) as to whether the measured sound pressure levels (in dBA) When the measured sound levels are outside of a threshold for safe dBA exposure levels for the human ear (i.e., dictated by health and safety agencies), then the alert mechanism is activated and the user/wearer of the SHP device and/or others observing the user/wearer are alerted to the dangerous dBA level exposures (Step 412).

If the measured sound levels are within the threshold of healthy and safe dBA exposure levels, then the process moves to Step 414, where measurements (acoustic) data is displayed on the display screen in dB(A) in order to monitor measurements, record data and assess recommended sound exposure limits.

At any point during the method of FIG. 4, the 2-way radio reception may be used by the user/wearer to communicate with a control center without removing the hearing protection. As described above, 2-way radio may use WLAN communication with access points.

Figure 5:
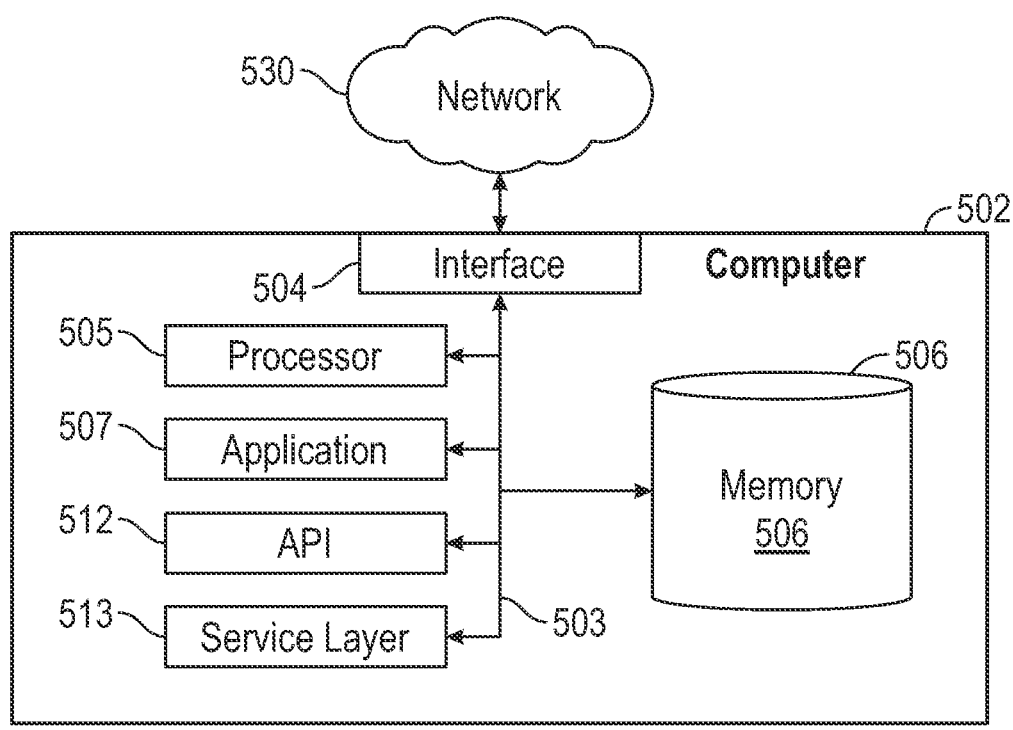
FIG. 5 shows a computing device in accordance with one or more embodiments.

Embodiments may be implemented on a computer system. FIG. 5 is a block diagram of a computing device (502) (i.e., a computer system) used to provide computational functionalities associated with described algorithms, methods, functions, processes, flows, and procedures as described in the instant disclosure, according to an implementation. Specifically, the illustrated computer (502) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (502) may include a computer that includes an input device, such as a keypad, keyboard, touch screen, or other device that can accept user information, and an output device that conveys information associated with the operation of the computer (502), including digital data, visual, or audio information (or a combination of information), or a GUI.

The computer (502) can serve in a role as a client, network component, a server, a database or other persistency, or any other component (or a combination of roles) of a computer system for performing the subject matter described in the instant disclosure. The illustrated computer (502) is communicably coupled with a network (530). In some implementations, one or more components of the computer (502) may be configured to operate within environments, including cloud-computing-based, local, global, or other environment (or a combination of environments).

At a high level, the computer (502) is an electronic computing device operable to receive, transmit, process, store, or manage data and information associated with the described subject matter. According to some implementations, the computer (502) may also include or be communicably coupled with an application server, e-mail server, web server, caching server, streaming data server, business intelligence (BI) server, or other server (or a combination of servers).

The computer (502) can receive requests over network (530) from a client application (for example, executing on another computer (502)) and responding to the received requests by processing the said requests in an appropriate software application. In addition, requests may also be sent to the computer (502) from internal users (for example, from a command console or by other appropriate access method), external or third-parties, other automated applications, as well as any other appropriate entities, individuals, systems, or computers.

Each of the components of the computer (502) can communicate using a system bus (503). In some implementations, any or all of the components of the computer (502), both hardware or software (or a combination of hardware and software), may interface with each other or the interface (504) (or a combination of both) over the system bus (503) using an application programming interface (API) (512) or a service layer (513) (or a combination of the API (512) and service layer (513). The API (512) may include specifications for routines, data structures, and object classes. The API (512) may be either computer-language independent or dependent and refer to a complete interface, a single function, or even a set of APIs. The service layer (513) provides software services to the computer (502) or other components (whether or not illustrated) that are communicably coupled to the computer (502). The functionality of the computer (502) may be accessible for all service consumers using this service layer. Software services, such as those provided by the service layer (513), provide reusable, defined business functionalities through a defined interface. For example, the interface may be software written in JAVA, C++, or other suitable language providing data in extensible markup language (XML) format or other suitable format. While illustrated as an integrated component of the computer (402), alternative implementations may illustrate the API (512) or the service layer (513) as stand-alone components in relation to other components of the computer (502) or other components (whether or not illustrated) that are communicably coupled to the computer (502). Moreover, any or all parts of the API (512) or the service layer (513) may be implemented as child or sub-modules of another software module, enterprise application, or hardware module without departing from the scope of this disclosure.

The computer (502) includes an interface 504). Although illustrated as a single interface (504) in FIG. 5, two or more interfaces (504) may be used according to particular needs, desires, or particular implementations of the computer (502). The interface (504) is used by the computer (502) for communicating with other systems in a distributed environment that are connected to the network (530). Generally, the interface (504 includes logic encoded in software or hardware (or a combination of software and hardware) and operable to communicate with the network (530). More specifically, the interface (504) may include software supporting one or more communication protocols associated with communications such that the network (530) or interface's hardware is operable to communicate physical signals within and outside of the illustrated computer (502).

The computer (502) includes at least one computer processor (505). Although illustrated as a single computer processor (505) in FIG. 5, two or more processors may be used according to particular needs, desires, or particular implementations of the computer (502). Generally, the computer processor (505) executes instructions and manipulates data to perform the operations of the computer (502) and any algorithms, methods, functions, processes, flows, and procedures as described in the instant disclosure. For example, measurements (acoustic data in dB(A)) may be displayed on the interface (504) which may be a display screen, for example, in order to monitor measurements, record data and assess recommended sound exposure limits.

The computer (502) also includes a memory (506) that holds data for the computer (502) or other components (or a combination of both) that can be connected to the network (530). For example, memory (506) can be a database storing data consistent with this disclosure. Although illustrated as a single memory (506) in FIG. 5, two or more memories may be used according to particular needs, desires, or particular implementations of the computer (502) and the described functionality. While memory (506) is illustrated as an integral component of the computer (502), in alternative implementations, memory (506) can be external to the computer (502).

The application (507) is an algorithmic software engine providing functionality according to particular needs, desires, or particular implementations of the computer (502), particularly with respect to functionality described in this disclosure. For example, application (507) can serve as one or more components, modules, applications, etc. Further, although illustrated as a single application (507), the application (507) may be implemented as multiple applications (507) on the computer (502). In addition, although illustrated as integral to the computer (502), in alternative implementations, the application (507) can be external to the computer (502).

There may be any number of computers (502) associated with, or external to, a computer system containing computer (502), each computer (502) communicating over network (530). Further, the term "client," "user," and other appropriate terminology may be used interchangeably as appropriate without departing from the scope of this disclosure. Moreover, this disclosure contemplates that many users may use one computer (502), or that one user may use multiple computers (502).

In some embodiments, the computer (502) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed:
1. A method, comprising:
   wearing, by a user, a smart hearing protection (SHP) device, wherein the SHP device is operatively connected to an ear of the user, and wherein the user is located in a harsh industrial environment with high noise levels created by a noise source located external the SHP device and the human ear, wherein the SHP device is an in-ear device;

measuring, by at least one internal sensor disposed on an external surface of the SHP device between the SHP device and the human ear, a sound pressure exposure level inside the ear of the user, wherein the sound pressure exposure level inside the ear of the user is sound pressure from the noise source that has been reduced by the SHP device;

measuring, by at least one external sensor disposed on an outer side of the SHP device and configured to measure a sound pressure level external to the SHP device, wherein the sound pressure level external to the SHP device is sound pressure from the noise source that has not been reduced by the SHP device;

wirelessly transmitting data including the measured sound pressure exposure level inside the ear of the user and the measured sound pressure level external to the SHP device to a smart hearing software application, wherein the smart hearing software application stores the data and monitors the sound pressure exposure level inside the ear of the user;

comparing the measured sound pressure exposure level inside the ear of the user to a sound pressure level safety threshold;

determining whether the measured sound pressure exposure level exceeds the sound pressure level safety threshold based on the comparison and using machine learning algorithms; and sending an alert signal to the SHP device, when the measured sound pressure exposure level exceeds the sound pressure level safety threshold.

2. The method of claim 1, further comprising: displaying results of the comparison on a display for review by occupational health and safety personnel.

3. The method of claim 1, further comprising: measuring, by an external sensor disposed on an inner side of the SHP device, a sound pressure exposure level external to the SHP device.

4. The method of claim 1, wherein the SHP device is connected wirelessly to a server hosting the smart hearing software application.

5. The method of claim 1, wherein the smart hearing software application comprises:

a repository configured to store sensor data received from both the internal and external sensors and sound pressure level threshold data;

a monitoring mechanism to monitor the sound pressure levels measured by the internal and external sensors in real-time; and an alert mechanism configured to send an alert signal to the SHP device, wherein the machine learning algorithms are configured to use the sensor data as training data and to learn to automate the process of determining whether measured sound pressure levels are unsafe.

6. The method of claim 5, further comprising, automating the determination of whether the measured sound pressure exposure level exceeds the sound pressure level safety threshold based on the comparison using the machine learning algorithms of the smart hearing software application.

* * * * *